United States Patent
Lu et al.

(10) Patent No.: US 8,383,337 B2
(45) Date of Patent: Feb. 26, 2013

(54) METHODS USING METAL OXIDE PARTICLES FOR ANALYTE DETECTION

(75) Inventors: Su Lu, Shanghai (CN); Li Zhu, Clifton Park, NY (US); Zhida Pan, Shanghai (CN); Liangliang Qiang, Shanghai (CN); John Yupeng Gui, Acton, MA (US)

(73) Assignee: General Electric Company, Niskayuna, NY (US)

( * ) Notice: Subject to any disclaimer, the term of this patent is extended or adjusted under 35 U.S.C. 154(b) by 467 days.

(21) Appl. No.: 12/175,673

(22) Filed: Jul. 18, 2008

(65) Prior Publication Data

US 2010/0015633 A1 Jan. 21, 2010

(51) Int. Cl.
*C12Q 1/68* (2006.01)
*C07H 21/04* (2006.01)
*C07K 5/00* (2006.01)

(52) U.S. Cl. .......... 435/6.1; 435/7.1; 536/23.1; 530/300

(58) Field of Classification Search .................. None
See application file for complete search history.

(56) References Cited

U.S. PATENT DOCUMENTS

| | | | | |
|---|---|---|---|---|
| 4,313,734 A * | 2/1982 | Leuvering | ..................... | 436/525 |
| 4,889,798 A * | 12/1989 | Rabbani | ........................... | 435/6 |
| 7,045,364 B2 * | 5/2006 | Limoges et al. | ............. | 436/525 |
| 7,176,036 B2 | 2/2007 | Wang et al. | | |
| 7,312,040 B2 | 12/2007 | Roitman | | |
| 2004/0014073 A1 | 1/2004 | Trau et al. | | |
| 2004/0058389 A1 | 3/2004 | Wang et al. | | |
| 2006/0003457 A1 * | 1/2006 | Porter et al. | .................... | 436/56 |
| 2009/0053694 A1 * | 2/2009 | Kriksunov | ........................ | 435/6 |

FOREIGN PATENT DOCUMENTS

WO 02/12888 A3 2/2002
WO WO 02/082078 * 10/2002

OTHER PUBLICATIONS

Murielle Dequaire, Chantal Degrand, and Benoit Limoges; An Electrochemical Metalloimmunoassay Based on a Colloidal Gold Label; Web Release Date: Oct. 21, 2000; Anal. Chem., 72(22), 5521-5528.
Joseph Wang; Nanoparticle-Based Electrochemical DNA Detection; Analytica Chimica,Acta, 2003, 500:247-257.
Nora Graf and Roland Kramer; Enzymatic amplification in a bioinspired, autonomous signal cascade; Royal Society of Chemistry 2008; Chem. Commun., 2006, 4375-4376.
Joseph Wang; Nanoparticle-Based Amplified Transduction of Biomolecular Interactions; pp. 1036-1043; Small, 2005, 1(11):1036-1043.
Nora Graf, Mareike Goritz and Roland Kramer; A Metal-Ion-Releasing Probe for DNA Detection by Catalytic Signal Amplification; Angew. Chem. Ind. 2006, 45:4013-4015.
Hongquan Zhang, Qiang Zhao, Xing-Fang Li and X. Chris Le; Ultrasensitive assays for proteins; Analyst, 2007, 132, 724-737.
Search Report and Written Opinion from corresponding PCT Application No. PCT/EP2009/059153 dated Nov. 26, 2009.

(Continued)

*Primary Examiner* — Betty Forman
(74) *Attorney, Agent, or Firm* — Jenifer W. Haeckl (57) ABSTRACT

A method includes binding a probe to an analyte present in a sample, wherein the probe comprises a binder bonded to a metal particle that is capable of releasing metal ions when contacted with a reagent solution. The method includes contacting the metal particle with the reagent solution to release the metal ions, and observing an optical signal from the released metal ions to determine a presence or amount of the analyte in the sample. An associated kit is also provided.

22 Claims, 5 Drawing Sheets

OTHER PUBLICATIONS

Zhu et al., "DNA hybridization at magnetic nanoparticles with electrochemical stripping detection" Electroanalysis, vol. 16, No. 23, pp. 1925-1930, Dec. 2004.

Fan et al., "Magnetic bead-based chemiluminescent metal immunoassay with a colloidal gold label", vol. 77, No. 10, pp. 3238-3242, May 15, 2005.

Li et al., "A chemiluminescent metalloimmunoassay based on silver deposition on colloidal gold labels", vol. 359, No. 2, pp. 247-252, Dec. 15, 2006.

Choi et al., "Semi-quantitative analysis for selecting Fe- and Zn-dense genotypes of staple food crops", vol. 20, No. 6, pp. 496-505, Jun. 8, 2007.

* cited by examiner

METHODS USING METAL OXIDE PARTICLES FOR ANALYTE DETECTION

BACKGROUND

1. Technical Field

The invention includes embodiments that relate to methods for detecting an analyte. The invention includes embodiments that relate to a kit for detecting an analyte.

2. Discussion of Related Art

Detection of chemical and biological analytes may be required in various applications, for example, in pharmaceutical research, clinical diagnostics, food and beverage-quality monitoring, water purification, soil, water, and air-pollution monitoring, or in detection of chemical or biological warfare agents.

A chemical or biological analyte may be detected using molecules (probes) capable of specifically recognizing the analyte. Recognition may occur via highly specific interactions between two molecules, for example, an enzyme and a substrate, antibody and antigen, and the like. An occurrence or non-occurrence of the recognition reaction may be detected using suitable detection means as indication of the presence or absence of the analyte. In some applications, the analyte may be present in a very low concentration and the recognition event between the probe and the analyte may not be easily detected. Analyte amplification techniques may be employed to increase the concentration of the analyte, which may make it difficult to accurately quantify the analyte. In some analyte detection techniques, the recognition between the probe and the analyte may be partial or may not be completely specific resulting in false positives.

It may be desirable to have a method for detection of an analyte that differs from those methods that are currently available. It may be desirable to have a kit for detection of an analyte that has characteristics or properties that differ from those that are currently available.

BRIEF DESCRIPTION

In one embodiment, a method includes binding a probe to an analyte that may be present in a sample. The probe includes a binder bonded to a metal particle. The probe can release metal ions when contacted with a reagent solution. The method includes contacting the metal particle with the reagent solution to release the metal ions, and observing an optical signal from the released metal ions to determine a presence or amount of the analyte in the sample.

In one embodiment, a method includes binding a probe to at least one analyte if such is present in a sample. The probe includes a binder that is bonded to a zinc particle. The method further includes contacting the zinc particle with an acid solution to release zinc cations, and optically detecting the released zinc cations.

In one embodiment, a kit includes a composition for optically detecting an analyte. The composition includes a probe including a binder bonded to a metal particle, a reagent solution capable of releasing metal ions from the metal particle, and one or more ligands capable of binding to the metal ions to form one or more optically detectable metal complexes.

DETAILED DESCRIPTION

The invention includes embodiments that relate to methods for detecting an analyte. The invention includes embodiments that relate to a kit for detecting an analyte.

As used herein, the term "peptide" refers to a linear sequence of amino acids connected to each other by peptide bonds between the alpha amino and carboxyl groups of adjacent amino acids. The amino acids may be the standard amino acids or some other non standard amino acids. Some of the standard nonpolar (hydrophobic) amino acids include alanine (Ala), leucine (Leu), isoleucine (Ile), valine (Val), proline (Pro), phenylalanine (Phe), tryptophan (Trp) and methionine (Met). The polar neutral amino acids include glycine (Gly), serine (Ser), threonine (Thr), cysteine (Cys), tyrosine (Tyr), asparagine (Asn) and glutamine (Gln). The positively charged (basic) amino acids include arginine (Arg), lysine (Lys) and histidine (His). The negatively charged (acidic) amino acids include aspartic acid (Asp) and glutamic acid (Glu). The non standard amino acids may be formed in body, for example by post-translational modification, some examples of such amino acids being selenocysteine and pyrolysine. The peptides may be of a variety of lengths, either in their neutral (uncharged) form or in forms such as their salts. The peptides may be either free of modifications such as glycosylations, side chain oxidation or phosphorylation or comprising such modifications. Substitutes for an amino acid within the sequence may also be selected from other members of the class to which the amino acid belongs. A suitable peptide may also include peptides modified by additional substituents attached to the amino side chains, such as glycosyl units, lipids or inorganic ions such as phosphates as well as chemical modifications of the chains. Thus, the term "peptide" or its equivalent may be intended to include the appropriate amino acid sequence referenced, subject to the foregoing modifications, which do not destroy its functionality.

As used herein, the term "carbohydrate" refers to a polyhydroxy aldehyde or ketone, or a compound that can be derived from them by any of several means including (1) reduction to give sugar alcohols; (2) oxidation to give sugar acids; (3) substitution of one or more of the hydroxyl groups by various chemical groups, for example, hydrogen may be substituted to give deoxysugars, and amino group ($NH_2$ or acetyl-NH) may be substituted to give amino sugars; (4) derivatization of the hydroxyl groups by various moieties, for example, phosphoric acid to give phosphor sugars, or sulphuric acid to give sulfo sugars, or reaction of the hydroxyl groups with alcohols to give monosaccharides, disaccharides, oligosaccharides, and polysaccharides. Carbohydrate group may include monosaccharides, disaccharides, or oligosaccharides. Suitable monosaccharides may include, but are not limited to, glucose, fructose, mannose and galactose. A disaccharide, as further defined herein, is a compound that yields two molecules of a monosaccharide upon hydrolysis. Suitable disaccharides may include, but are not limited to, lactose, maltose, isomaltose, trehalose, maltulose, and sucrose. Suitable oligosaccharides may include, but are not limited to, raffinose and acarbose. Also included are the saccharides modified by additional substituents, for example, methyl glycosides, N-acetyl-glucosamine, N-acetyl-galactosamine and their de-acetylated forms.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and $F(ab')_2$, or Fab'). In addition, aggregates, polymers, and conjugates of immunoglobulins or their fragments may be used where appropriate so long as binding affinity for a particular molecule is substantially maintained.

The invention includes a method in one embodiment. The method includes binding a probe to an analyte present in a sample, wherein the probe includes a binder bonded to a metal particle that is capable of releasing metal ions when contacted with a reagent solution. The method further includes contacting the metal particle with the reagent solution to release the metal ions, and observing an optical signal from the released metal ions to determine a presence or amount of the analyte in the sample. In one embodiment, the method may be used to detect one or more analytes in a sample.

As used herein, the term "probe" may refer to an agent having a binder and a metal particle. As used herein, the term "binder" may refer to a chemical or a biological molecule that may selectively bond to an analyte. A suitable binder may be selected depending on the sample to be analyzed and the analytes available for detection in the sample. In one embodiment, an analyte to be detected may be essentially biological in nature and the binder may include a biological molecule. A biological molecule may refer to a molecule obtained from a biological subject in-vivo or in-vitro. Suitable biological molecules may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, antigens, haptens, vitamins, and the like.

In one embodiment, a binder may recognize and bind to the analyte. For example, an analyte may include a nucleic acid and the binder may include an oligonucleotide sequence capable of binding to a complementary base sequence in the nucleic acid. In one embodiment, an analyte may include a protein and the binder may be capable of binding to one or more amino acids in the protein sequence. In one embodiment, an analyte may include a ligand and the binder may include a receptor capable of binding to the analyte. Alternatively, an analyte may include a receptor and the binder may include a ligand. In one embodiment, an analyte may include an antigen and the binder may include an antibody or antibody fragment or vice versa. In one embodiment, an analyte may include a nucleic acid the binder may include complementary nucleic acids. In one embodiment, the analyte and the binder may include proteins capable of binding to each other.

A probe includes a metal particle bonded to the binder. In one embodiment, a suitable metal particle may be selected such that the metal particle may be responsive to a reagent solution to release metal ions. In one embodiment, a metal particle may include elemental metal or metal compounds. In one embodiment, a metal particle may include a metal oxide or a mixed metal oxide. In one embodiment, a metal particle may essentially include a metal oxide. In one embodiment, a metal particle may include zinc oxide.

A metal particle may be characterized by one or more of average particle sizes, particle shapes, or particle cross-sectional geometries. In one embodiment, a metal particle may include a metal nanoparticle. Nanoparticle as used herein refers to particles having an average particle size on the nano scale. A nanoparticle may have a largest dimension (for example, a diameter or length) in the range of from about 1 nanometer to about 1000 nanometers.

In one embodiment, an average particle size of the metal particle may be in a range of less than about 1 nanometer. In one embodiment, an average particle size of the metal particle may be in a range of from about 1 nanometer to about 10 nanometers, from about 10 nanometers to about 25 nanometers, from about 25 nanometers to about 50 nanometers, from about 50 nanometers to about 75 nanometers, or from about 75 nanometers to about 100 nanometers. In one embodiment, an average particle size of the metal particle may be in a range of from about 100 nanometers to about 200 nanometers, from about 200 nanometers to about 400 nanometers, from about 400 nanometers to about 600 nanometers, from about 600 nanometers to about 800 nanometers, or from about 800 nanometers to about 1000 nanometers.

In one embodiment, a metal particle may include a metal microparticle. Microparticle as used herein refers to particles having an average particle size on the micron scale. A microparticle may have a largest dimension (for example, a diameter or length) of at least 1 micrometer. In one embodiment, an average particle size of the metal particle may be in a range of from about 1 micrometer to about 5 micrometers, from about 5 micrometers to about 10 micrometers, from about 10 micrometers to about 25 micrometers, or from about 25 micrometers to about 50 micrometers. In one embodiment, a metal particle size may be selected depending on the amount of signal amplification required.

A metal particle may have a variety of shapes and cross-sectional geometries that may depend, in part, upon the process used to produce the particles. In one embodiment, a metal particle may have a shape that is a sphere, a rod, a tube, a flake, a fiber, a plate, a wire, a cube, or a whisker. A metal particle may include particles having two or more of the aforementioned shapes. In one embodiment, a cross-sectional geometry of the particle may be one or more of circular, ellipsoidal, triangular, rectangular, or polygonal. In one embodiment, a metal particle may consist essentially of non-spherical particles. For example, such particles may have the form of ellipsoids, which may have all three principal axes of differing lengths, or may be oblate or prelate ellipsoids of revolution. Non-spherical nanoparticles may alternatively be laminar in form, wherein laminar refers to particles in which the maximum dimension along one axis is substantially less than the maximum dimension along each of the other two axes. Such laminar nanoparticles may have a shape similar to the tabular silver halide. Non-spherical nanoparticles may also have the shape of frusta of pyramids or cones, or of elongated rods. In one embodiment, the metal particle may be irregular in shape. In one embodiment, the metal particle may consist essentially of spherical particles.

In one embodiment, a binder and a metal particle may be bonded to each other via a linker. A linker may include a form of linking structure or sequence formed due to the non-covalent or covalent bond formation. Non-covalent interactions may include, but are not limited to, hydrophobic interactions, ionic interactions, hydrogen-bond interactions, high affinity interactions (such as, biotin-avidin or biotin-streptavidin complexation), or other affinity interactions. The nature of the binding may be such that it does not substantially impair the effectiveness of either entity (for example, binding mechanism should not affect the metal particle dissociability or analyte-binding capability of the binder).

In one embodiment, a metal-particle may include one or more functional groups capable of binding to the binder. Correspondingly, a binder may include a complementary functional group capable of reacting with the functional group of the metal particle. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioethers; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones; hydroxyamine and aldehydes or ketones; imido ester and amines or anilines; isocyanate and amines or anilines; and isothiocyanate and amines or anilines. A functional group in one of the aforementioned functional group pair may be present in the metal particle and a corresponding functional group may be present in the binder. For example, a metal particle may include a carboxylic acid-functional group and the probe may include an amine, aniline, alcohol or acyl halide, or vice versa. Conjugation between the metal particle and the binder may be effected in this case by formation of an amide or an ester linkage. In one embodiment, linkage between the metal particle and the binder may be affected using ligand-receptor pairs, for example, biotin-streptavidin. A binder may be bonded to a biotin, a metal particle may be bonded to a streptavidin, and the binder-metal particle binding may be provided by biotin-streptavidin pair formation. In one embodiment, a metal particle may include one or more amine functional groups capable of bond formation with the binder.

In one embodiment, a suitable functional group may be included in the metal particle in-situ, that is, during the synthesis of the metal particle. In one embodiment, a metal particle may be further functionalized with a suitable functional material to provide one or more functional groups on the surface prior to bonding the metal particle with the binder component. In one embodiment, a method may include steps of functionalizing the metal particle, binding the functionalized metal particle to a binder to form a probe, and binding the probe to the analyte. In one embodiment, a method may include the steps of binding the binder to the analyte, and binding the binder to the metal particle.

In one embodiment, the analyte may be a portion of a sample to be analyzed. Suitable samples that may be analyzed using the compositions disclosed herein may include soil samples, air samples, water samples, plant samples, food samples, or biological samples. "Biological sample" as used herein, may refer to a sample obtained from a biological subject in-vivo or in-vitro. In some embodiments, a biological sample may be of an eukaryotic origin, for example, insects, protozoa, birds, fish, reptiles, and in another embodiment of a mammalian origin, for example, rat, mouse, cow, dog, donkey, guinea pig, or rabbit, and in another embodiment of a primate origin, for example, chimpanzees or humans. Suitable examples of biological samples may include cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. Biological samples also may include extracts from a biological sample, for example, an antigen from a biological fluid, such as blood.

A sample may include any of the aforementioned samples regardless of their physical condition, such as, but not limited to, being frozen or stained or otherwise treated. In some embodiments, a sample may include compounds which are not naturally intermixed with the sample in nature such as preservatives, anticoagulants, buffers, fixatives, nutrients, antibiotics, solvents, or the like. In one embodiment, the sample may be immobilized on a solid support, such as, blots, assays, arrays, glass slides, nanoparticles, beads, microtiter, ELISA plates, or any other substrate.

In some embodiments, the sample may be analyzed as is, that is, without harvest and/or isolation of the analyte of interest. In an alternate embodiment, harvest and isolation of analytes may be performed prior to analysis. An analyte according to an embodiment of the invention may be present on the surface of a sample (for example, an antigen on a surface of a tissue section) or present in the bulk of the sample (for example, an antibody in a buffer solution). In some embodiments, an analyte may not be inherently present on the surface of a sample and the sample may have to be processed to make the analyte available on the surface. In one embodiment, a sample may not be required and the analyte may be analyzed directly or the analyte may be directly immobilized on a substrate during analysis.

In one embodiment, a method may include a step of analyte or sample preparation. Analyte or sample preparation may include one or more of the following steps: separation of analyte, concentration of analyte, purification of analyte, analyte amplification, and the like. One or more of the aforementioned analyte or sample preparation techniques may be employed to make the analyte available for binding and detection.

In one embodiment, a method may further include immobilizing an analyte on a surface of a substrate. A method may further include a blocking step in which the substrate (if employed) may be contacted with reagents that may block non-specific binding of the first probe and the second probe to the substrate. A method may also include one or more washing steps after contacting the analyte with the probe. A washing step may include contacting the analyte-probe complex with a series of washing solutions to remove any unbound or non-specifically bound probes.

In one embodiment, a method may further include magnetically separating the analyte-probe complex before contacting the metal particle with the reagent solution. Magnetic separation of the analyte-probe complex may provide for greater sensitivity and specificity by reducing the possibility of any signal from the unbound probes. In one embodiment, an analyte may be contacted with a magnetic particle before binding the analyte to the probe. Accordingly, the resulting analyte-probe metal complex may be separated from any unbound probes by magnetically separating the analyte-probe complex. In another embodiment, a probe may be bonded to a magnetic particle in addition to the metal particle. After binding the probe to the analyte, the resulting probe-analyte complex may be separated by magnetic separation.

Suitability of analyte(s) to be analyzed may be determined by the type and nature of analysis required for the sample. In one embodiment, the analysis may provide information about the presence or absence of an analyte in the sample. For example, the analysis may provide information about the presence or absence of a germ or pathogen in a suspected, infected air sample. In another embodiment, an analysis may provide information on a state of a sample. For example, if the sample includes a drinking water sample, the analysis may provide information about the concentration of bacteria in the sample and thus the potability of the sample. Similarly, if the sample includes a tissue sample, the methods disclosed herein may be used to detect analyte(s) that may help in comparing different types of cells or tissues, comparing different developmental stages, detecting the presence of a disease or abnormality, determining the type of disease abnormality or investigating the interactions between multiple analytes and pathways.

In one embodiment, an analyte may include one or more biological agents. Suitable biological agents may include pathogens, toxins, or combinations thereof. Biological agents may include prions, microorganisms (viruses, bacteria or fungi), some unicellular and multicellular eukaryotes (for example parasites), or their associated toxins. Pathogens are infectious agents that may cause disease or illness to their host (animal or plant). Pathogens may include one or more of bacteria, viruses, protozoa, fungi, parasites, or prions.

Some examples of bacterial biological agents (and the diseases or effect caused by them) may include one or more of *Escherichia coli* (peritonitis, food poisoning), *Mycobacterium tuberculosis* (tuberculosis), *Bacillus anthracis* (anthrax), *Salmonella* (food poisoning), *Staphylococcus aureus* (toxic shock syndrome), *Streptococcus pneumoniae* (pneumonia), *Streptococcus pyogenes* (strep throat), *Helicobacter pylori* (stomach ulcers), or *Francisella tularensis* (tularemia).

Some examples of viruses (and the diseases or effect caused by them) may include one or more of hepatitis A, B, C, D or E (liver disease), influenza virus (flu, Avian flu), SARS coronavirus (severe acute respiratory syndrome), herpes simplex virus (herpes), molluscum contagiosum (rash), or human immunodeficiency virus (AIDS).

Some examples of protozoa (and the diseases or effect caused by them) may include one or more of cryptosporidium (cryptosporidiosis), giardia lamblia (giardiasis), plasmodium (malaria), or trypanosoma cruzi (chagas disease). Some examples of fungi (and the diseases or effect caused by them) may include one or more of pneumocystis jiroveci (opportunistic pneumonia), tinea (ringworm), or candida (candidiasis).

Some examples of parasites may include one or more of roundworms, scabies, tapeworms, or flatworms. Some examples of protein-based pathogens may include prions (Bovine spongiform encephalopathy (BSE) commonly known as mad cow disease or variant Creutzfeldt-Jakob disease (vCJD)).

Toxins include proteins capable of causing disease on contact or absorption with body tissues by interacting with biological macromolecules and may be used as bio-weapons. Suitable toxins may include Ricin, SEB, Botulism toxin, Saxitoxin, and Mycotoxins. Some other examples of diseases caused by biological agents may include anthrax, Ebola, Bubonic Plague, Cholera, Tularemia, Brucellosis, Q fever, Machupo, Coccidioides mycosis, Glanders, Melioidosis, Shigella, Rocky Mountain Spotted Fever, Typhus, Psittacosis, Yellow Fever, Japanese B Encephalitis, Rift Valley Fever, or Smallpox.

Biological agents may be present in food samples, in air samples, in water samples, in soil samples, in plant samples, or in biological samples. In one embodiment, biological agents may provide information regarding the spoilage of food samples, for example, the bacteria in a spoilt meat sample. In one embodiment, the biological agents may indicate the presence or concentration of legionella pneumophila in an industrial water sample (cooling, water, process water, or waste water). In one embodiment, the biological agents may indicate the presence or concentration of cryptosporidia giardia in a municipal water sample (drinking water or waste water). In one embodiment, the biological agents may indicate the presence or concentration of lysteria or *salmonella* in a food sample.

In one embodiment, the biological agents may be used as biological warfare agents. Detection and analysis of the biological agents may provide information regarding the infected area. In one embodiment, analysis of the biological agents may provide information regarding the effectiveness of disinfection of the affected environment.

In one embodiment, an analyte that may be detected using the compositions disclosed herein, may include one or more biomolecules. In one embodiment, a biomolecule-based analyte may be part of a biological agent, such as a pathogen. In one embodiment, a biomolecule may be used for diagnostic, therapeutic, or prognostic applications, for example, in RNA or DNA assays. Suitable biomolecules may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, vitamins, antigens, or haptens. The term analyte refers to both separate molecules and to portions of such molecules, such as an epitope of a protein that may bind specifically with one or more binders.

Binders and their corresponding biomolecule analytes may be considered as binding pairs, of which non-limiting examples may include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, and peptide nucleic acid sequences); Protein A/antibody; Protein G/antibody; nucleic acid/nucleic acid binding protein; or polynucleotide/polynucleotide binding protein.

Binding between the binder and the analyte may be effected by non-covalent bond formation or covalent bond formation. Covalent bond formation may refer to chemical bond formation (reaction) between the analyte and the probe resulting from sharing of one or more electrons between two or more atoms (in the analyte and the probe). Non-covalent bond formation may refer to interactions between the probe and the analyte that are not covalent in nature. Suitable examples of non-covalent interactions may include one or more ionic interactions, hydrophobic bonding, dipole-dipole interactions, hydrogen bonding, Van der Waal interactions, or high affinity interactions (such as, biotin-avidin or biotin-streptavidin complexation). In some embodiments, the analyte and the binder may have areas on their surfaces or in cavities giving rise to specific recognition between the two resulting in non-covalent binding. In some embodiments, a binder may bind to an analyte based on the reciprocal fit of a portion of their molecular shapes.

The binder may bind to the analyte in a specific manner. As used herein, the term "specific binding" may refer to the specific recognition of one of two different molecules for the other compared to substantially less recognition of other molecules. In some embodiments, the binder may bind to an analyte with sufficient specificity, that is, a binder may bind to an analyte with greater affinity than it does to any other molecule. In some embodiments, the binder may bind to other molecules, but the binding may be such that the non-specific binding may be at or near background levels. In some embodiments, the affinity of the binder for the analyte of interest may be in a range that is at least 2-fold, at least 5-fold, at least 10-fold, or more than its affinity for other molecules. In some embodiments, binders with the greatest differential affinity may be employed, although they may not be those with the greatest affinity for the analyte. In some embodiments, a binder molecule may have an intrinsic equilibrium association constant (KA) for the analyte no lower than about $10^5$ $M^{-1}$ under physiological-equivalent conditions, such as a pH of about 6 to about 8 and temperature ranging from about 0 degrees Celsius to about 37 degrees Celsius.

In one embodiment, a binder may be sequence or structure-specific, wherein the sequence or structure of an analyte recognized and bound by the binder may be sufficiently unique to that analyte.

In one embodiment, a binder may be structure-specific and may recognize a primary, secondary, or tertiary structure of an analyte. A primary structure of an analyte may include specification of its atomic composition and the chemical bonds connecting those atoms (including stereochemistry), for example, the type and nature of linear arrangement of amino acids in a protein. A secondary structure of an analyte may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of an analyte may be is its overall three dimensional structure. A quaternary structure of an analyte may be the structure formed by its noncovalent interaction with one or more other analytes or macromolecules (such as protein interactions). An example of a quaternary structure may be the structure formed by the four-globin protein subunits to make hemoglobin. A binder in accordance with the embodiments of the invention may be specific for any of the aforementioned structures.

An example of a structure-specific binder may include a protein-specific molecule that may bind to a protein analyte. Examples of suitable protein-specific molecules may include antibodies and antibody fragments, nucleic acids (for example, aptamers that recognize protein analytes), or protein substrates (non-catalyzable). In some embodiments, an analyte may include an antigen and the binder may include an antibody. A suitable antibody may include monoclonal antibodies, polyclonal antibodies, multispecific antibodies (for example, bispecific antibodies), or antibody fragments so long as they bind specifically to an antigen analyte.

In one embodiment, the binder may be specific for a region of the analyte of interest. For example, the binder may be specific for a protein modification. Protein modifications may include post-translational modifications such as phosphorylation, glycosylation, ubiquitinylation, acetylation, and the like.

In one embodiment, a binder may be sequence-specific. A sequence-specific binder may include a nucleic acid and the binder may be capable of recognizing a particular linear arrangement of nucleotides or derivatives thereof in the analyte. In some embodiments, the linear arrangement may include contiguous nucleotides or derivatives thereof that may each bind to a corresponding complementary nucleotide in the probe. In an alternate embodiment, the sequence may not be contiguous as there may be one, two, or more nucleotides that may not have corresponding complementary residues on the probe. Suitable examples of nucleic acid-based probes may include, but are not limited to, DNA or RNA oligonucleotides or polynucleotides. In some embodiments, suitable nucleic acids may include nucleic acid analogs, such as dioxygenin dCTP, biotin dcTP 7-azaguanosine, azidothymidine, inosine, or uridine.

In one embodiment, both the binder and the analyte may include nucleic acids. In one embodiment, a nucleic-acid based binder may form a Watson-Crick bond with the nucleic acid analyte. In another embodiment, the nucleic acid binder may form a Hoogsteen bond with the nucleic acid analyte, thereby forming a triplex. A nucleic acid binder that binds by Hoogsteen binding may enter the major groove of a nucleic acid analyte and hybridize with the bases located there. Suitable examples of the above binders may include molecules that recognize and bind to the minor and major grooves of nucleic acids (for example, some forms of antibiotics.) In certain embodiments, the nucleic acid binders may form both Watson-Crick and Hoogsteen bonds with the nucleic acid analyte (for example, bis PNA probes are capable of both Watson-Crick and Hoogsteen binding to a nucleic acid).

The length of nucleic acid probe binder also determine the specificity of binding. The energetic cost of a single mismatch between the probe and the nucleic acid analyte may be relatively higher for shorter sequences than for longer ones. In some embodiments, hybridization of smaller nucleic acid probes may be more specific than the hybridization of longer nucleic acid probes, as the longer binders may be more amenable to mismatches and may continue to bind to the nucleic acid depending on the conditions. In certain embodiments, shorter binders may exhibit lower binding stability at a given temperature and salt concentration. In some embodiments, the nucleic acid binder may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the nucleic acid binder may have a length in a range that is greater than about 1000 nucleotides. Notwithstanding the length of the nucleic acid binder, all the nucleotide residues of the binder may not hybridize to complementary nucleotides in the nucleic acid analyte. For example, the binder may include 50 nucleotide residues in length, and only 25 of those nucleotide residues may hybridize to the nucleic acid analyte. In some embodiments, the nucleotide residues that may hybridize may be contiguous with each other. The nucleic acid probes may be single stranded or may include a secondary structure.

Regardless of the type of binder and the analyte, the specificity of binding between the binder and the analyte may also depend on the binding conditions (for example, hybridization conditions in case of complementary nucleic acids). Suitable binding conditions may be realized by modulation of one or more of pH, temperature, probe concentration, or salt concentration.

In one embodiment, a probe may be capable of binding to the analyte through combination of one or more intermediatory binders. The combinations of binders may provide greater specificity or in certain embodiments amplification of the signal. Thus, in one embodiment, a method may include additional binders that may be used to form a sandwich with the first binder. In one embodiment, the first binder (bonded to the metal particle) may be capable of binding to a corresponding primary binder, which in turn may be capable of binding to the analyte. The first binder in this case may then be referred to as secondary binder. In one embodiment, the first binder may be capable of binding to a corresponding secondary binder which in turn may be capable of binding to a corresponding primary binder which may be capable of binding to the analyte. The first binder in this case may then be referred to as tertiary binder.

Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-HisG for recombinant protein with His-Tag epitope, mouse anti-xpress for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for α-D-galactose; and melibiose for carbohydrate-binding proteins, sugars, nickel couple matrix or heparin.

In some embodiments, a combination of a primary antibody and a secondary antibody may be used as a first binder. A primary antibody may be capable of binding to a specific region of the analyte and the secondary antibody may be capable of binding to the primary antibody. A secondary antibody may be attached to a metal particle before binding to the primary antibody or may be capable of binding to the metal particle at a later step. In an alternate embodiment, a primary antibody and specific binding ligand-receptor pairs (such as biotin-streptavidin) may be used. The primary antibody may be attached to one member of the pair (for example biotin) and the other member (for example, streptavidin as a first probe) may be bonded with a metal particle. In some embodiments, initial signal amplification may be obtained when several secondary antibodies may bind to epitopes on the primary antibody.

Further signal amplification may be obtained by contacting the metal particle with a reagent solution to release metal ions. A reagent solution may include one or more chemical agents capable of releasing metal ions from the metal particle. In one embodiment, suitable reagents solutions may include agents that modify pH (for example, acids or bases), electron donors (e.g., nucleophiles), electron acceptors (e.g., electrophiles), oxidizing agents, reducing agents, or combinations thereof. In one embodiment, a reagent solution may include an acid. In one embodiment, a reagent solution is a mineral acid. Non-limiting examples of suitable mineral acids include nitric acid, sulfuric acid or hydrochloric acid. In one embodiment, a reagent solution includes a buffer solution having a specific pH. In one embodiment, a reagent solution may have a pH in a range of about 3 to about 5.

One or more of the aforementioned chemical agents may be used in the methods disclosed herein depending upon the susceptibility of the metal particle, of the binder, of the analyte, or of the biological sample to the chemical agent. In some embodiments, a chemical agent that essentially does not affect the integrity of the binder, the analyte, and the biological sample may be employed. In some embodiments, a chemical agent that does not affect the specificity of binding between the binder and the analyte may be employed.

In one embodiment, a method may include contacting the released metal ions with one or more ligands to form a metal complex. A suitable ligand may include an organic or an inorganic molecule capable of forming a metal complex with one or more released metal ions. In one embodiment a metal complex formed may be capable of providing an optical signal. In some embodiments, a metal complex may be light-emissive. A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence.

In one embodiment, a suitable ligand may include a calorimetric probe for metal ions, that is, a ligand may include a molecule capable of forming a metal complex with the released metal ions that provides a color. In one embodiment, a suitable ligand may include a fluorescent probe for metal ions, that is, a ligand may include a molecule capable of forming a fluorescent metal complex with the released metal ions. In one embodiment, a suitable ligand may include a fluorescent probe or a calorimetric probe for $Zn^{2+}$ ions. In one embodiment, a suitable calorimetric probe may include 4-(2-pyridylazo) resorcinol.

In one embodiment, a method may include observing an optical signal from the one or more metal complexes. In one embodiment, a method may include observing a fluorescent signal from the one or more metal complexes. In one embodiment, a method may include observing a calorimetric signal from the one or more metal complexes.

In some embodiments, signal intensity, signal wavelength, signal location, signal frequency, or signal shift may be determined using one or more of the optical detection techniques. In some embodiments, one or more aforementioned characteristics of the signal may be observed, measured, and recorded.

In one embodiment, an optical signal may be analyzed to obtain information regarding the analyte. In one embodiment, the method may include correlating the signal to a type of an analyte. In one embodiment, the method may include correlating the signal to an amount of analyte. In one embodiment, the method may include correlating the signal to both type and amount of an analyte.

In some embodiments, an intensity value of a signal (for example, fluorescence intensity) may be measured and may be correlated to the amount of analyte in the sample. A correlation between the amount of analyte and the signal intensity may be determined using calibration standards. In one embodiment, the method may include determining the relative concentration or absolute amount of an analyte in a sample. The relative concentration or amount may be determined by measuring the amount of signal from probes bound to an analyte.

In embodiments where multiple analytes may be analyzed using multiple probes, relative amounts of different analytes in the biological sample may be determined by measuring different signal intensities. In some embodiments, one or more control samples may be used. By observing a presence or absence of a signal in the samples (sample of interest versus a control), information regarding the sample may be obtained. For example by comparing a diseased tissue sample versus a normal tissue sample, information regarding the analytes present in the diseased tissue sample may be obtained. Similarly by comparing signal intensities between the samples (i.e., sample of interest and one or more controls), information regarding the expression of analytes in the sample may be obtained.

In one embodiment, a location of the signal in the sample may be observed. In some embodiments relative locations of two or more signals may be observed. A location of the signal may be correlated to a location of the analyte, providing information regarding localization of different analytes in the sample. In some embodiments, an intensity value of the signal and a location of the coincident signal may be correlated to obtain information regarding localization of different analytes in the sample. For examples certain analytes may be expressed more in the cytoplasm relative to the nucleus in a tissue sample, or vice versa. In some embodiments, information regarding relative localization of analytes may be obtained by comparing location and intensity values of two or more signals.

In one embodiment, one or more of the observing or the correlating steps may be performed using computer-aided means. In some embodiment, one or more of the method steps be automated and may be performed using automated systems.

In one embodiment, a method is provided. The method includes binding a probe to at least one analyte present in a sample, wherein the probe includes a binder coupled to a zinc particle. The method further includes contacting the zinc particle with an acid solution to release zinc cations, and optically detecting the released zinc cations. In one embodiment, the zinc particle includes zinc oxide. In one embodiment, the zinc particle includes one or more amine functional groups. In one embodiment, the probe includes biotin and the analyte includes streptavidin.

In one embodiment, a kit is provided. A kit includes a composition for optically detecting an analyte. The composition includes a probe having a binder bonded to a metal particle. The composition includes a reagent solution capable of releasing metal ions from the metal particle. The composition includes one or more ligands capable of binding to the metal ions to form one or more optically detectable metal complexes.

In one embodiment, the method and kit disclosed herein may be particularly applicable for detecting analytes in a rare or small sample (for example, a nanoliter volume sample) or in a sample where analyte concentration is low. In one embodiment, the test sample or the analyte sample may have a nanoliter volume, that is, it may be only necessary to load a nanoliter volume into the detection system in order to perform the method described herein.

In one embodiment, the method and kit disclosed herein may be particularly applicable for detecting an analyte at a nanomolar concentration. In one embodiment, the methods as disclosed herein may be particularly applicable for detecting an analyte at a picomolar concentration. In one embodiment, the methods as disclosed herein may be particularly applicable for detecting an analyte at a femtomolar concentration. In one embodiment, the methods as disclosed herein have an analyte detection limit that is less than about 10-18 moles. In one embodiment, the methods as disclosed herein have an analyte detection limit that is less than about 10-20 moles. In one embodiment, the methods as disclosed herein have an analyte detection limit that is less than about $10^{-21}$ moles.

In one embodiment, an analyte may be present at a frequency of less than about 1 in 10,000 molecules. In one embodiment, an analyte may be present at a frequency of less than about 1 in 1,00,000 molecules. In one embodiment, an analyte may be present at a frequency of less than about 1 in 1,000,000 molecules. In one embodiment, an analyte may be present at a frequency of less than about 1 in 2,000,000 molecules in the test sample. Accordingly, the methods may be used to detect and analyze analytes that are extremely rare.

In one embodiment, the method and kit disclosed herein may provide for detection of analytes at low concentrations by amplifying the observable signal using the metal ions released from the metal particles. In one embodiment, the methods disclosed herein may provide for detection of analytes at low concentrations by amplifying the observable signal, thus obviating the need to amplify the analyte using techniques such as polymerase chain reaction (PCR). In one embodiment, the methods disclosed herein may provide for detection of analytes that may not be amenable to analyte amplification techniques like PCR, for example, protein analytes.

In one embodiment, the method and kit disclosed herein may provide for detection of multiple analytes in a test sample, thereby conserving sample. In one embodiment, the degree of multiplexing may be 2 (i.e., 2 analytes may be detected in a single analysis). In one embodiment, the degree of multiplexing may in a range of from about 2 to about 4, from about 4 to about 6, from about 6 to about 10, from about 10 to about 20, from about 20 to about 50, from about 50 to about 100, from about 100 to about 250, or from about 250 to about 500. In one embodiment, the degree of multiplexing may be greater than about 500.

In one embodiment, the method and kit disclosed herein may provide a detectable signal in a test time in a range of less than about 2 hours, in a range of less than about 1 hour, in a range of less than about 30 minutes, in a range of less than about 15 minutes, or in a range of less than about 5 minutes.

EXAMPLES

The following examples do not impose limitations upon the claims. Unless specified otherwise, ingredients are commercially available from such common chemical suppliers as Aldrich Chemical Company (Milwaukee, Wis.).

Example 1

Surface Functionalization of a Metal Particle (ZnO Particle)

Zinc Oxide (ZnO) particles are used as a metal particle (99.9%, powder, <1 micrometer (µm) particle size). Reacting the ZnO particles functionalizes the surface of the ZnO particle. Particularly, amine group functionalization of the ZnO particle surface is performed as follows: 0.6 grams (g) of zinc oxide particle and 2 milliliters (mL) of 3-aminopropyl triethoxysilane (APTES) dissolves in 15 ml ethanol (EtOH) to make an initial solution. The initial solution is vigorously stirred overnight. Solvent is removed by centrifuge. The particles are washed twice with 20 mL of ethanol. The final product is an amine-functionalized ZnO particle that is suspended in 12 mL ethanol (50 milligram (mg)/mL in EtOH).

Example 2

Synthesis of a Biotin-ZnO Probe

The amine-functionalized ZnO particle of Example 1 is conjugated with Biotin-3-sulfo-N-hydroxysuccinimide ester sodium salt (NHS-Biotin; commercially available from Sigma Aldrich and from Thermo Fisher Scientific Inc. (Rockford, Ill.)) to form a biotin-based probe. In particular, 100 microliters (uL) of amine-functionalized ZnO particle (50 mg/mL in EtOH) is suspended in 1 mL Phosphate-Buffered Saline (PBS buffer) to form a buffered amine-functionalized ZnO particle solution. A quantity of 1 mg of NHS-Biotin dissolves in 1 mL of ethanol and is added to the buffered, amine functionalized ZnO particle solution to form a second solution. The second solution is allowed to react for 18 hours at standard room temperature and pressure.

The solvent is removed from the reacted second solution and the particles are washed with PBS buffer three times. The washed particles are re-suspended in 1 mL of PBS buffer containing 8% glutaraldehyde to form a suspension. The suspension is mixed for 2 hours on a rocking shaker and is centrifuged for 2 minutes at 10,000 rpm. After centrifuging, the supernatant is discarded. The particles are then re-suspended in PBS buffer, and are centrifuged as mentioned above. The re-suspension and centrifugation process are repeated twice, to form a particulate slurry.

The particulate slurry is then re-suspended in 1 mL of PBS solution, and 1 mL of ethanolamine (EA) is added to form an EA suspension. The EA suspension is mixed for 30 minutes on a rocking shaker. The solvent is removed by centrifugation to leave a slurry of particles. The particle slurry is washed with PBS buffer twice, and is dispersed and suspended in 1 mL of PBS solution containing 10% BSA (Bovine Serum Albumin).

The suspended particle slurry in 10% BSA-PBS solution is mixed on a rocking shaker at 1000 cycles per minute overnight. After centrifugation at 10000 rpm, the supernatant is discarded, and the particle is re-suspended in 0.5% BSA-PBS solution with 0.1% sodium azide. The reaction product includes metal particle (ZnO)-attached biotin probe (Biotin-ZnO probe). The reaction product is stored at 4 degrees Celsius until needed.

Example 3

Synthesis of a ZnO Control Particles

A quantity of 100 uL of amine-functionalized ZnO particle (50 mg/mL in EtOH) is suspended in 1 mL PBS buffer to form a buffered amine-functionalized ZnO particle solution. The solvent is removed from the buffered amine-functionalized ZnO particle solution, and the particles are washed with PBS buffer three times. The washed particles are re-suspended in 1 mL of PBS buffer containing 8% glutaraldehyde to form a suspension. The suspension is mixed for 2 hours on a rocking shaker and centrifuged for 2 minutes at 10,000 rpm. After centrifuging, the supernatant is discarded. The particles are re-suspended in PBS buffer, and are centrifuged as described above. The re-suspension and centrifugation processes are repeated twice to form particulate slurry.

The particulate slurry is re-suspended in 1 mL of PBS solution, and 1 mL of ethanolamine (EA) is added to form an EA suspension. The EA suspension is mixed for 30 minutes on a rocking shaker. The solvent is removed by centrifugation to leave a slurry of particles. The particle slurry is washed with PBS buffer twice, dispersed and suspended in 1 mL of PBS solution containing 10% BSA.

The suspended particle slurry in 10% BSA-PBS solution is mixed on a rocking shaker at 1000 cycles per minute overnight. After centrifugation at 10000 rpm, the supernatant is discarded and the particle is re-suspended in 0.5% BSA-PBS solution with 0.1% sodium azide. The reaction product includes ZnO control particles. The reaction product is stored at 4 degrees Celsius until needed.

Example 4

Figure 1:
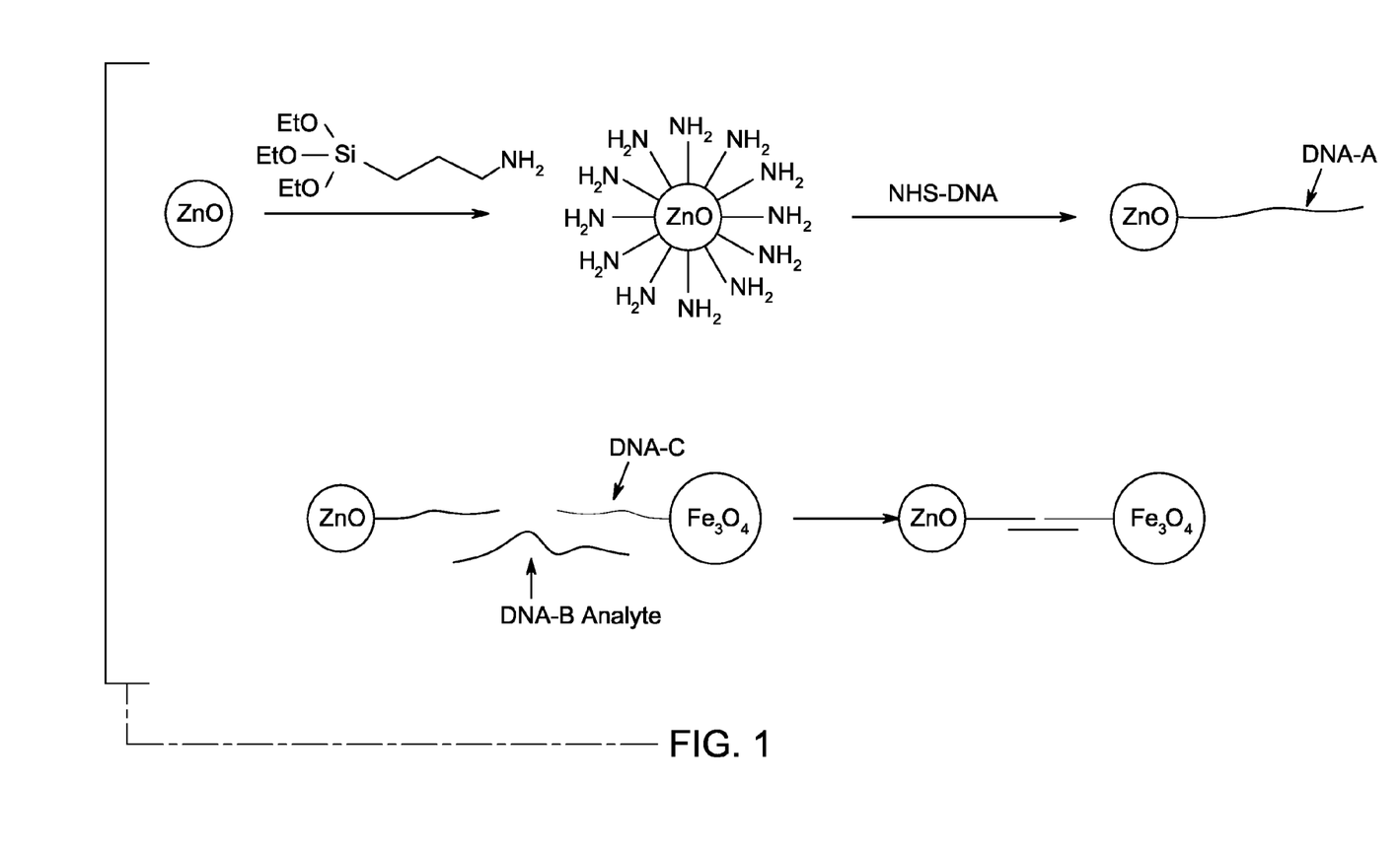
FIG. 1 is a schematic illustration of method of detecting a nucleic acid analyte according to one embodiment of the invention.
Figure 2:
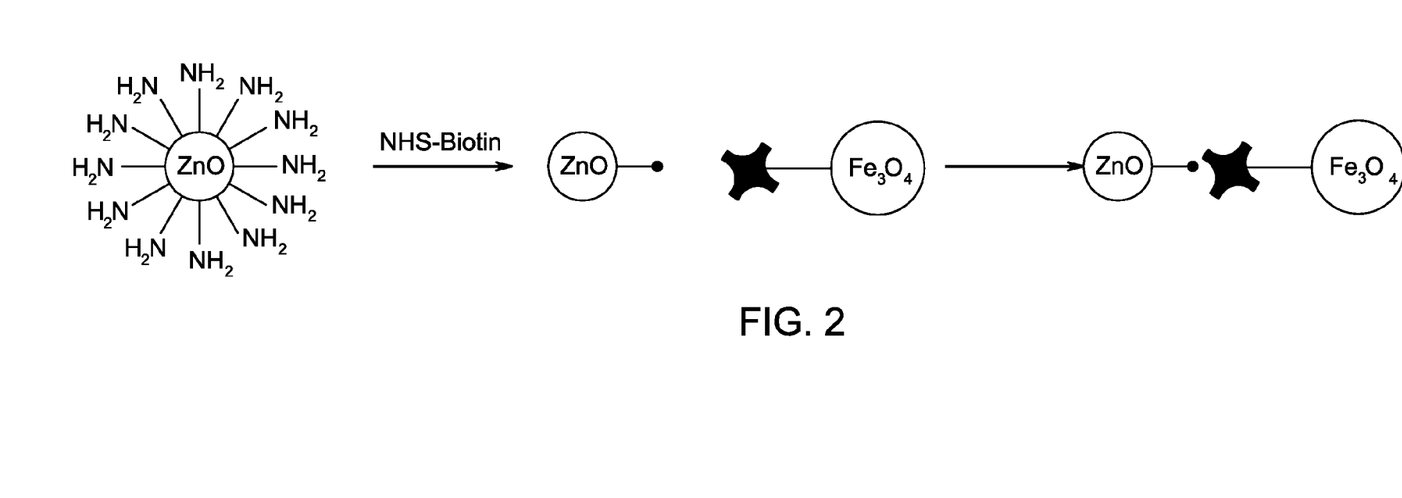
FIG. 2 is a schematic illustration of method of detecting streptavidin analyte according to one embodiment of the invention.

Capture of Biotin-ZnO Probe with Magnetic Streptavidin Particle, and Release and Detection of $Zn^{2+}$ Cation from Captured Biotin-ZnO Probe The ZnO-bonded biotin probe contacts the streptavidin analyte as shown in FIG. 2. In particular, 2 uL Biotin-ZnO probe (concentration 50 mg/mL in ethanol) is added to 100 uL of magnetic particle attached with a Streptavidin group (Streptavidin-Iron Oxide particle) used as obtained. The solvent is removed by centrifugation at 1000 rpm for 10 hours to form a pellet. The pellet is re-suspended in 300 uL of PBS buffer. The solution containing the suspended particles is incubated on a rocking shaker for 30 minutes. The tube containing the suspended particles is inserted into a DYNAL magnetic separator. After 3 minutes, supernatant is removed, and 500 microliters of PBS buffer containing 0.05 percent TWEEN 20 is added to the tube. Supernatant is again removed and the above-described process is repeated five times to yield a particulate slurry. The particulate slurry is then re-suspended in 300 uL of PBS buffer, and is centrifuged for 2 minutes at 10000 rpm. Supernatant is discarded to yield a sample. Sample includes Biotin-ZnO probe captured by the Streptavidin-attached magnetic particle.

A similar procedure is followed to yield a control sample for comparison. The control particles are not surface functionalized as per the above process. In particular, 2 microliters of a mixture of ZnO control particle (concentration 50 mg/mL in ethanol) is added to 100 uL of magnetic particle attached with a Streptavidin. The solvent is removed, and the pellet is re-suspended in 300 uL of PBS buffer. The solution containing the suspended particles is incubated on a rocking shaker for 30 minutes. The tube containing the suspended particles is inserted into a DYNAL magnetic separator. After 3 minutes, supernatant is removed and 500 uL of PBS buffer having 0.05% TWEEN 20 is added to the tube. Supernatant is again removed and the above-described process is repeated five times to yield particulate slurry. The particulate slurry is then re-suspended in 300 uL of PBS buffer, and is centrifuged for 2 min at 10000 rpm. Supernatant is discarded to yield the control. The control includes Streptavidin-Iron Oxide and does not have any metal particle (ZnO particle).

The sample and the control are each, separately, treated with 20 uL solution of 0.1 M sulfuric acid ($H_2SO_4$). Treatment with $H_2SO_4$ releases exposed or susceptible $Zn^{2+}$ cations from the metal oxide particle (ZnO particle) into the solutions. The solutions are shaken for 3 minutes on a rocking shaker and are centrifuged at 10000 rpm for 2 minutes. The supernatant from the control tube and the sample tube each is transferred to new, individual tubes. A calorimetric probe, ZINCON detects released $Zn^{2+}$ cations by generating a Zincon-$Zn^{2+}$ complex. Supernatant from the control and the sample (2 microliters each) is each separately added into a 0.002M ZINCON solution in water. Each solution is incubated for 5 minutes at room temperature and then is read by a UV spectrometer.

Figure 3:
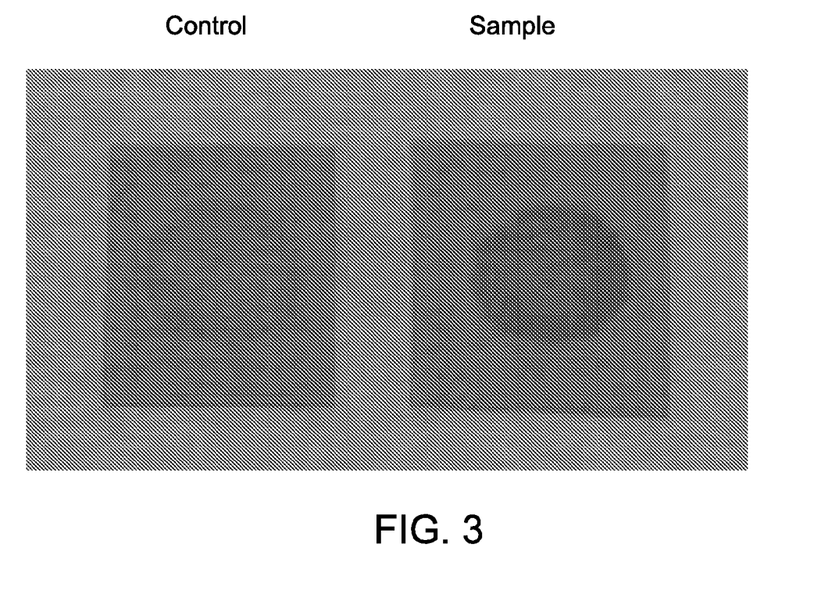
FIG. 3 shows a pictograph of a sample detected using zinc oxide particle.

FIG. 3 illustrates a pictograph in which the sample shows an amplified, positive signal due to the release of $Zn^{2+}$ ions from the ZnO particles when compared to the control. As shown in UV spectrograph in FIG. 4, the solution containing supernatant from the sample contained zinc ions, and shows a new peak at 640 nm. The peak at ~640 nm results from the ZINCON-$Zn^{2+}$ complex. However, the solution containing the supernatant from the control does not show any peak at ~640 nm. Rather, the spectrum reveals a ZINCON absorbance peak at ~490 nm. The supernatant from control does not contain zinc ions and the ZnO control particles are not captured by the magnetic Streptavidin particles during the magnetic separation step.

The order of signal amplification obtained using ZnO particles is calculated by determining the volume of a ZnO particle and the corresponding mass of the ZnO particle. The number of $Zn^{2+}$ cations per particle is calculated based on the molecular weight of ZnO and density of zinc oxide. A 1-micrometer ZnO particle corresponds to a particle volume of about $5.23 \times 10^{-19}$ $m^3$, and a particle mass of about $2.9 \times 10^{-12}$ g (ZnO density is 5.61 $g/cm^3$). The number of zinc atoms per ZnO particle is then determined to be about $2.2 \times 10^{10}$ (ZnO $M_w = 81.39$, $3.56 \times 10^{-14}$ mol). For every ZnO particle employed in the probe, ten orders of signal amplification should be possible using a 1-micrometer particle. Similarly, a 50-nanometer ZnO particle corresponds to about $2.8 \times 10^6$ zinc atoms.

Analyte detection limit is calculated by determining the concentration of zinc atoms in a given volume of solution and the known detection limit of the colorimetric/fluorescent probe used for $Zn^{2+}$ ions. Assuming a volume of 50 microliters, a 1-micrometer ZnO particle corresponds to a concentration of about $7.1 \times 10^{-10}$ mol/l (0.7 nM). Assuming a detection limit of the Zn-probe to be about 10 nM, a DNA detection limit may be calculated to be about 15 DNA molecules (0.1 zmole). Similarly, a 50 nm particle corresponds to a DNA detection limit of about 150,000 DNA molecules.

Example 5

Analyte Detection Limit of Enzyme-Based Signal Amplification

HRP labeled Goat anti-mouse IgG antibody is used to calculate the detection limit of enzyme based amplification. A solution of 1 mg/mL antibody is employed as a stock solution, which is further diluted to 1:100 dilutions in 2% BSA PBS solution. The antibody is serially diluted across a 96-well plate from 1:100 solution in 2% BSA. A 50 μl of sample mixture (different concentration of HRP labeled Goat anti-mouse IgG antibody in 2% BSA) with 75 μl of TMB substrate is added to the plate for 30 minutes followed by addition 75 μl of stop solution (Elisa stop solution, commercially available from Aldrich). BSA blank (50 μl 2% BSA and 75 μl substrate) is used as a control sample.

Figure 4:
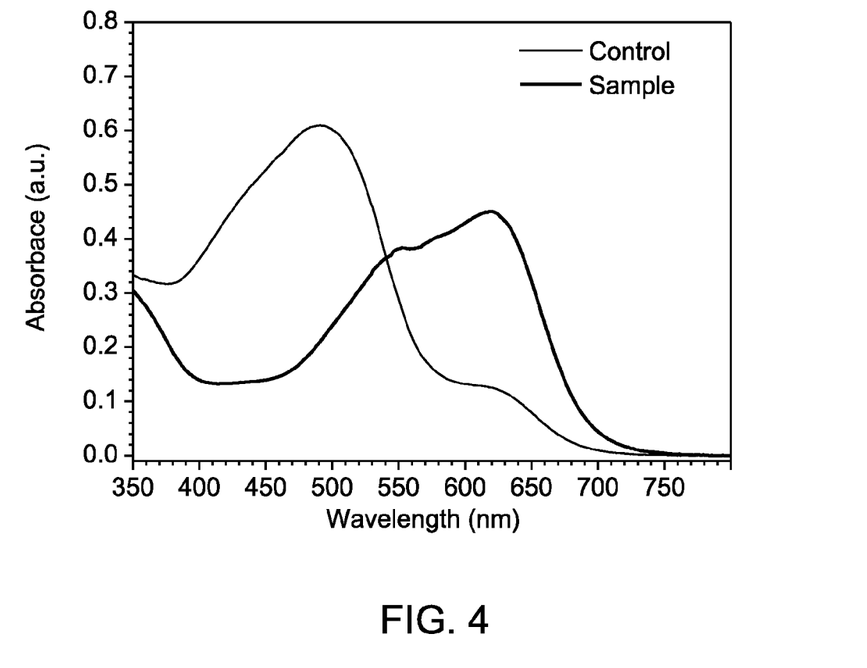
FIG. 4 shows the plots of absorbance of a sample detected using zinc oxide particle.

The plate is read at 430 nm by a VICTOR3 plate reader from PERKINELMER. FIG. 4 shows absorbance as a function of concentration. The detection limit is determined by noting the concentration at which a step change in absorbance is observed. A detection limit of about $7.6 \times 10^{-8}$ mg/mL is observed for HRP-labeled antibody. This corresponds to an analyte concentration of about $3.9 \times 10^{-13}$ mol/L (molecular weight of HRP labeled antibody is 194 kDa) or about 10,000,000 analyte species in a 50 μL sample solution; the assumption being that one HRP-linked antibody corresponds to one analyte.

Figure 5:
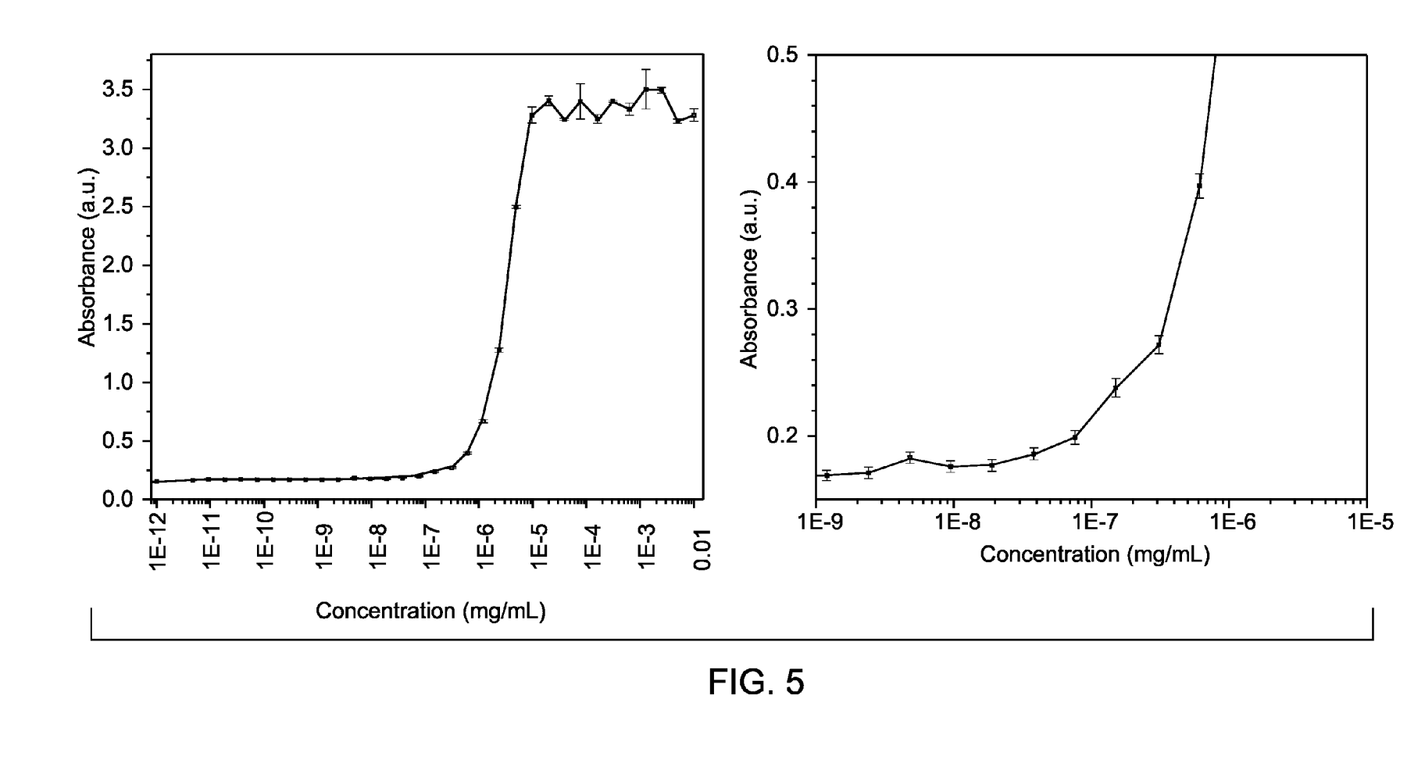
FIG. 5 shows the plots of absorbance as a function of concentration for enzyme-based analyte detection

FIG. 5 shows absorbance as a function of concentration for HRP labeled Goat anti-mouse IgG antibody. The detection limit is determined by noting the concentration at which a step change in absorbance is observed. A detection limit in the order of about $10^{-7}$ mg/mL is observed for HRP labeled antibody. This corresponds to an analyte concentration of about $5 \times 10^{-13}$ mol/L (molecular weight of HRP labeled antibody is 194 kDa. It is assumed that one antibody corresponds to one analyte and one HRP linked antibody. The two graphs in FIG. 5 are the same curves with different scale, indicating the detection limit of the HRP scheme.

Example 5

Analyte Detection Limit of Metal-Oxide Based Signal Amplification

A 1-micrometer Zinc Oxide particle solution (1 mg/mL in PBS buffer: Dissolved by 0.1 M sulfuric acid and serially diluted from a 1:100 solution) is used to calculate the detection limit of metal-oxide based signal amplification. The solution is serially diluted from a 1:100 solution. 0.1 M sulfuric acid is employed to dissolve ZnO and to release $Zn^{2+}$ ions. The released Zn ions are colorometrically detected by mixing 75 μl of solution having released $Zn^{2+}$ ions with 75 μl Zincon and analyzing by 3150 UV spectrometer (Shimadzu Corporation).

Figure 6:
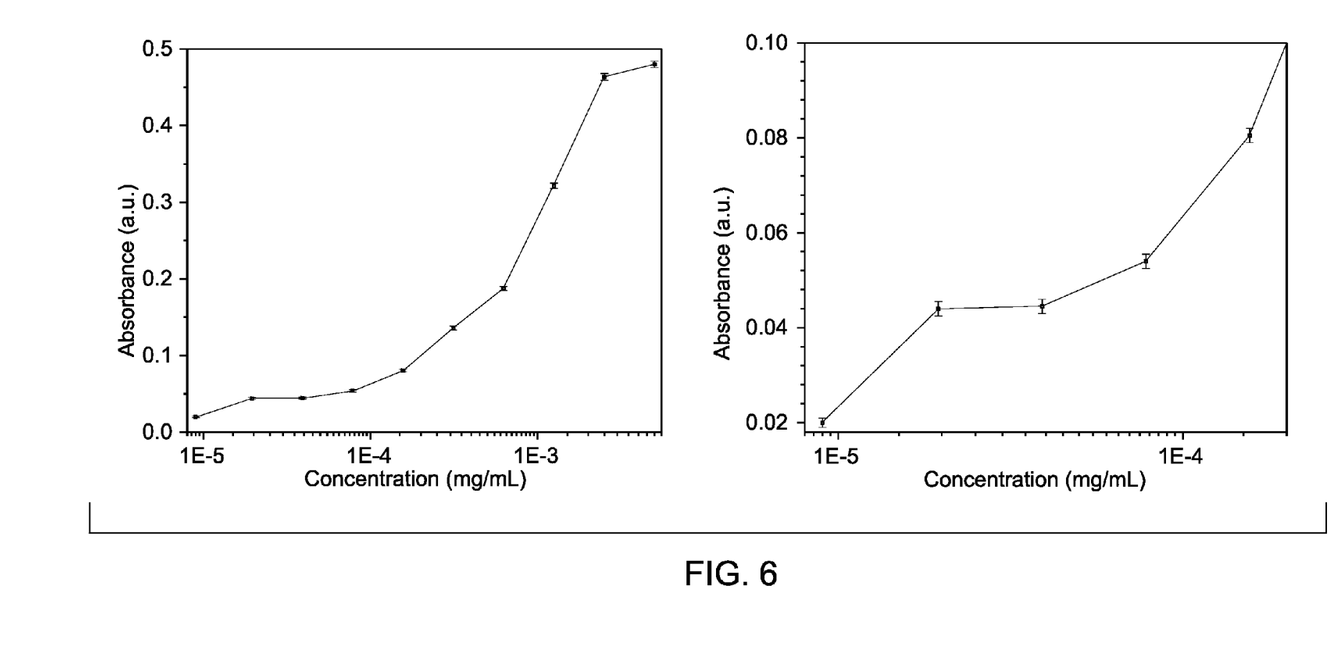
FIG. 6 shows the plots of absorbance as a function of concentration for metal-particle based analyte detection.

FIG. 6 shows absorbance as a function of concentration for $Zn^{2+}$ ions. The detection limit is determined by noting the concentration at which a step change in absorbance is observed. A detection limit of about $7.8 \times 10^{-5}$ mg/mL is observed for ZnO. This corresponds to an analyte concentration of about $4.5 \times 10^{-17}$ mol/L (molecular weight of 1 μm ZnO is $1.75 \times 10^{12}$) or about 2000 analyte species in a 75 μL sample solution; the assumption being that one ZnO particle corresponds to one analyte. A 1-micrometer ZnO is about 10,000 times more sensitive than ELIZA using the HRP enzyme. The two graphs in FIG. 6 are the same curves with different scale, indicating the detection limit of the ZnO particle scheme.

In the following specification and the clauses that follow, reference will be made to a number of terms that have the following meanings. The singular forms "a", "an" and "the" include plural referents unless the context clearly dictates otherwise. Approximating language, as used herein throughout the specification and clauses, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be".

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

The foregoing examples are illustrative of some features of the invention. The appended claims are intended to claim the invention as broadly as has been conceived and the examples herein presented are illustrative of selected embodiments from a manifold of all possible embodiments. Accordingly, it is Applicants' intention that the appended claims not limit to the illustrated features of the invention by the choice of examples utilized. As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges there between. It is to be expected that variations in these ranges will suggest themselves to a practitioner having ordinary skill in the art and, where not already dedicated to the public, the appended claims should cover those variations. Advances in science and technology may make equivalents and substitutions possible that are not now contemplated by reason of the imprecision of language; these variations should be covered by the appended claims.

What is claimed is:

1. A method, comprising:
    binding a probe to an analyte present in a sample, wherein the probe consists essentially of a binder bonded to a metal particle that is capable of releasing metal ions when contacted with a reagent solution;
    releasing the metal ions from the metal particle by contacting the metal particle with the reagent solution; and
    observing an optical signal from the released metal ions to determine a presence or amount of the analyte in the sample;
    wherein the metal particle consists essentially of a metal oxide.

2. The method as defined in claim 1, wherein the binder comprises one or more of nucleic acids, proteins, sugars, lipids, carbohydrates, vitamins, enzymes, or enzyme substrates.

3. The method as defined in claim 1, wherein the analyte comprises one or more of peptides, proteins, nucleic acids, polysaccharides, lipids, enzymes, enzyme substrates, antigens, haptens, aptamers, or vitamins.

4. The method as defined in claim 1, comprising binding the probe to the analyte through a binding mechanism having a binding constant that is greater than about $10^5$ $M^{-1}$ under physiological-equivalent conditions.

5. The method as defined in claim 1, further comprising a functional material disposed on the metal particle and which comprises one or more functional groups capable of bonding to the binder.

6. The method as defined in claim 5, wherein the functional group is an amine functional group.

7. The method as defined in claim 1, wherein the metal particle has an average particle size in a range of from about 1 nanometer to about 1000 nanometers.

8. The method as defined in claim 1, wherein the metal particle has an average particle size in a range of about 1 micrometer to about 50 micrometers.

9. The method as defined in claim 1, wherein the reagent solution comprises an acid.

10. The method as defined in claim 9, wherein the reagent solution has a pH in a range of about 3 to about 5.

11. The method as defined in claim 1, comprising contacting the metal ions with one or more ligands to form one or more metal complexes.

12. The method as defined in claim 11, comprising observing an optical signal from the one or more metal complexes.

13. The method as defined in claim 12, comprising observing a fluorescent signal from the one or more metal complexes.

14. The method as defined in claim 12, comprising observing a colorimetric signal from the one or more metal complexes.

15. The method as defined in claim 12, comprising measuring an intensity value of the optical signal.

16. The method as defined in claim 15, comprising correlating the intensity value to an amount of analyte.

17. The method as defined in claim 1, wherein the method has an analyte detection limit that is less than about $10^{-18}$ moles.

18. The method as defined in claim 1, wherein the method has an analyte detection limit that is less than about $10^{-21}$ moles.

19. The method as defined in claim 1, comprising magnetically separating the probe bonded to the analyte before contacting the metal particle with the reagent solution.

20. A method, consisting essentially of:
    binding a probe to at least one analyte present in a sample, wherein the probe consists essentially of a binder bonded to a zinc oxide particle;

releasing zinc cations from the zinc oxide particle by contacting the zinc oxide particle with an acid solution; and optically detecting the released zinc cations.

21. The method as defined in claim 20, wherein the zinc oxide particle comprises one or more amine functional groups.

22. The method as defined in claim 20, wherein the probe comprises biotin and the analyte comprises streptavidin.

* * * * *